United States Patent [19]

Stanghellini et al.

[11] Patent Number: 5,767,090
[45] Date of Patent: Jun. 16, 1998

[54] MICROBIALLY PRODUCED RHAMNOLIPIDS (BIOSURFACTANTS) FOR THE CONTROL OF PLANT PATHOGENIC ZOOSPORIC FUNGI

[75] Inventors: Michael E. Stanghellini; Raina Margaret Miller; Scott Lynn Rasmussen; Do Hoon Kim; Yimin Zhang, all of Tucson, Ariz.

[73] Assignee: Arizona Board of Regents, on behalf of the University of Arizona, Tucson, Ariz.

[21] Appl. No.: 588,213

[22] Filed: Jan. 17, 1996

[51] Int. Cl.$^6$ ............................................. A01N 43/16
[52] U.S. Cl. .......................... 514/23; 424/93; 424/93.41; 424/93.42; 424/93.43; 424/93.44; 424/93.45; 424/93.46; 424/93.47; 424/93.48; 435/252.3; 435/252.1
[58] Field of Search ................................ 424/93.47, 93.4, 424/93.41–93.48; 435/253.3, 252.1; 514/23

[56] References Cited

U.S. PATENT DOCUMENTS 4,996,049  2/1991  Haefele et al. ............................ 424/93

OTHER PUBLICATIONS

Becker, J.O., F.J. Schwinn (1993) "Control of Soil–borne Pathogens with Living Bacteria and Fungi: Status and Outlook" Pestic. Sci. 37:355–363.

Blakeman, J.P. (1982) "Phylloplane Interactions" Phytopathogenic Prokaryotes 1:307–333.

Guerra–Santos, L. et al. (1984) "*Pseudomonas aeruginosa* Biosurfactant Production in Continous Culture with Glucose as Carbon Source" Applied and Environmental Microbiology 48(2):301–305.

Herman, D.C. et al. (1995) "Removal of Cadmium, Lead, and Zinc from Soil by a Rhamnolipid Biosurfactant" Environmental Science & Technology 29(9):2280–2285.

Miller, R.A. (1995) "Biosurfactant–facilitated Remediation of Metal–contaminated Soils" Environmental Health Perspectives 103:59–62.

Rosenberg, E. (1986) "Microbial Surfactants" CRC Critical Reviews in Biotechnology 3(2):109–132.

Stanghellini, M.E., J.A. Tomlinson (1987) "Inhibitory and Lytic Effects of a Nonionic Surfactant on Various Asexual Stages in the Life Cycle of *Pythium* and *Phytophthora* Species" Phytopathology 77(1):112–114.

Stanghellini, M.E. et al. (1995) "Efficacy of nonionic surfactants in the control of zoospore spread of *Pythium aphanidermatum* in a recirculating hydroponic system" pp. 1–28.

Tomlinson, J.A., E.M. Faithfull (1979) "Effects of fungicides and surfactants on the zoospores of *Olpidium brassicae*" Ann. appl. Biol. 93:13–19.

Zhang, Y., R.M. Miller (1994) "Effect of Pseudomonas Rhamnolipid Biosurfactant on Cell Hydrophobicity and Biodegradation of Octadecane" Applied and Environmental Microbiology 60(6):2101–2106.

*Primary Examiner*—Robert A. Wax
*Assistant Examiner*—Nashaat T. Nashed
*Attorney, Agent, or Firm*—Saliwanchik, Lloyd & Saliwanchik

[57] ABSTRACT

Disclosed is the use of biosurfactants as biological control products. In particular, rhamnolipid biosurfactants produced by Pseudomonas spp. were demonstrated to rapidly kill zoospores by rupturing the plasma membrane of three representative zoosporic plant pathogenic microorganisms: *Pythium aphanidermatum*, *Plasmopara lactucae-radicis*, and *Phytophthora capsici*.

18 Claims, 2 Drawing Sheets

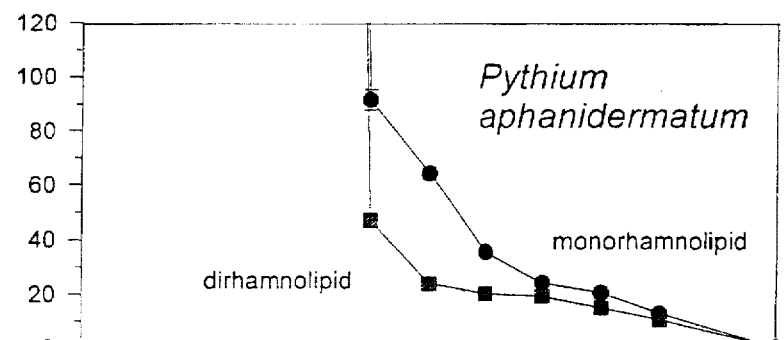
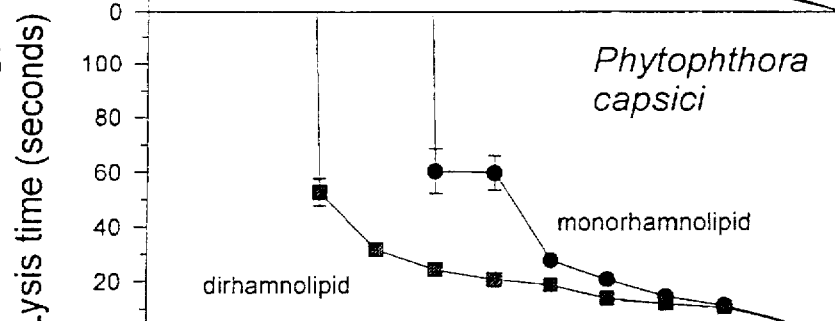
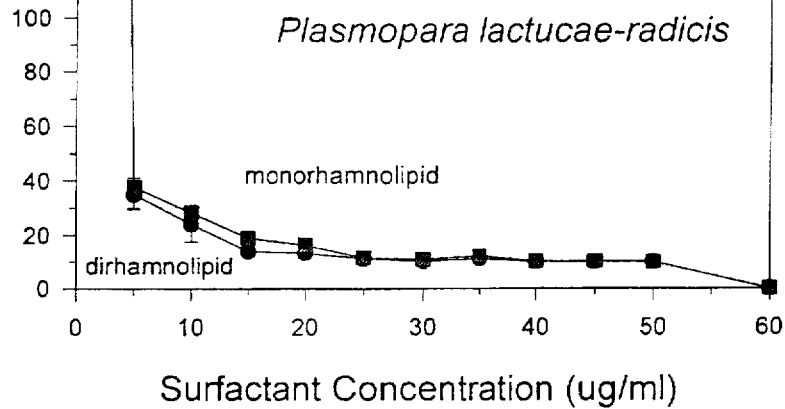

5,767,090

MICROBIALLY PRODUCED RHAMNOLIPIDS (BIOSURFACTANTS) FOR THE CONTROL OF PLANT PATHOGENIC ZOOSPORIC FUNGI

FIELD OF THE INVENTION

This invention pertains to the field of agriculture, in particular to the control of zoosporic plant pathogens.

BACKGROUND OF THE INVENTION

Alternative strategies to pesticide application are needed for the control of agriculturally important pests including plant pathogens, weeds, and insects. Such strategies will help address public concern regarding pesticide pollution, as well as the perception that pesticide residues on food pose a threat to human health. Of particular concern is the development of pesticide resistance. Alarm resulting from the growing incidence of pesticide resistance has prompted global efforts directed toward the search for alternate pest control strategies. One such strategy is biological control, which is the use of antagonistic microorganisms or microbial products to directly or indirectly control target pests.

Documented biological control mechanisms for plant pathogens include competition, hyperparasitism, predation, and the production of antimicrobial products such as antibiotics, hydrogen cyanide (HCN), and the siderophores (1). One diverse group of plant pathogenic microorganisms in particular need of control is collectively known as the zoosporic plant pathogens (2).

Among the more destructive zoosporic plant pathogens are the downy mildews (which are primarily associated with severe foliar diseases of many crops), and numerous species in the genus Pythium and Phytophthora which are destructive pathogens of roots, foliage, and fruits. One of the more notorious zoosporic pathogens is *Phytophthora infestans*, the cause of late blight of potato. Zoosporic plant pathogens share a common stage in their life cycle; a unicellular, motile, asexual spore known as the zoospore. The zoospore has been implicated as the primary, if not sole, infectious stage responsible for the costly epidemics caused by this group of plant pathogens. The one vulnerability of the zoospore is that this membrane-bound spore lacks a protective cell wall. In vitro studies have shown that some synthetic surfactants can destroy the permeability of the plasma membrane resulting in a loss of motility and rapid lysis of the zoospore (3,4). The same surfactants have little or no effect on other stages in the pathogen life cycle, including sporangia, chlamydospores, oospores, and hyphae, all of which have cells walls (3). Unfortunately, the synthetic surfactants that showed efficacy against zoospores are phenol-based and have not been registered as pesticides against zoosporic plant pathogens. Accordingly, there exists a need for an environmentally safe and effective method for controlling zoosporic plant pathogens.

SUMMARY OF THE INVENTION

It is an object of this invention to provide methods for controlling zoosporic plant pathogens by substantially reducing the spread and production of zoospores.

A further object of this invention is to provide a method of controlling zoosporic plant pathogens by using plant colonizing bacteria that produce anti-zoosporic rhamnolipid biosurfactants, and to identify strains of bacteria which are particularly advantageous in this method.

Yet another object of this invention is to provide a method of controlling zoosporic plant pathogens by application of certain anti-zoosporic biosurfactant compounds.

Biosurfactants which are produced by a variety of microorganisms have a great deal of structural diversity. Although the function of biosurfactants in nature is not yet clear, it has been speculated that they may play a role in: 1) enhancing bioavailability and biodegradation of slightly soluble organic carbon sources such as petroleum hydrocarbons, 2) attachment and detachment of bacteria to surfaces, or 3) antibacterial defense mechanisms (5). Biosurfactants have also been shown to complex metals efficiently, and may play a role in metal uptake or in reducing metal toxicity (6,7).

We have discovered that some leaf and root-inhabiting bacteria produce biosurfactants (Table 1), and these biosurfactant-producing bacteria, as well as culture supernatants from these biosurfactant-producing bacteria, cause the lysis of zoospores. However, not all biosurfactants have lytic activity against zoospores. For example, surfactin, a lipopeptide produced by another leaf epiphyte Bacillus spp., and a trehalose lipid (a glycolipid), produced by Rhodococcus spp., have little effect against zoospores, failing to cause lysis even at concentrations up to 1000 μg/ml. To prove that biosurfactants were the lytic agent responsible for the observed anti-zoosporic activity, biosurfactants were isolated from several Pseudomonas spp. (both fluorescent and non-fluorescent) and identified as glycolipids, more specifically a mixture of anionic mono- and dirhamnolipids. Identification of biosurfactant-induced rupture of the plasma membrane of zoospores as a new type of antagonistic mechanism, coupled with the activity against zoospores as a specific target, has significant implications for the control of destructive root and foliar diseases caused by zoosporic plant pathogens.

The subject invention can advantageously be used for the control of all zoosporic plant pathogens, which include the following genera: Plasmodiophora, Polymyxa, Spongospora, Physoderma, Olpidium, Synchytrium, Rhizophydium, Achlya, Aphanomyces, Albugo, Peronophthora, Pachymetra, Pythium, Phytophthora, Trachysphaera, Basidiophora, Bremia, Peronosclerospora, Plasmopara, Pseudoperonospora, Sclerophthora, Scierospora.

Use of these particular bacteria as a biological control agent, or use of the biosurfactants themselves, could substantially reduce the need for and use of synthetic fungicides. Approximately 80% of the $5.2 billion spent annually for fungicides in the U.S. are directed towards the control of foliar pathogens (9). However, to date, most of the research on biological control is directed towards seed and root diseases caused by soil-borne plant pathogens. This discrepancy in focus is attributed, in part, to the perception that the soil environment is more physically amenable to biological control than the leaf surface. Pseudomonas spp., however, occur widely as epiphytes on leaves (10). Our discovery that epiphytic biosurfactant-producing bacteria are also normal inhabitants of leaf and root surfaces, coupled with the discovery of the specific mechanism of antagonism against zoosporic pathogens, questions the validity of this perception. In particular, plants possessing Pseudomonas phylloplanal proliferation, plus Pseudomonas-produced products, provide promising, practical, plant pathogen protection potential. Accordingly, our invention includes the identification and use of certain bacteria, as well as compounds produced by these bacteria, in a method for controlling zoosporic plant pathogens.

BRIEF DESCRIPTION OF THE DRAWINGS

FIG. 2 shows rapidity of zoospore lysis of three species of zoosporic plant pathogens upon exposure to various concentrations of two biosurfactants (a mono- and a dirhamnolipid) produced by Pseudomonas spp. A 30 µl suspension of zoospores of each fungus, which contained not less than 600 zoospores, was mixed with 1 ml of sterile distilled water amended with the biosurfactants. The maximum time for cessation of motility and lysis of the entire zoospore population, timed with a stop watch and determined microscopically, was recorded for each fungus. Three separate experiments were performed and the data represent the average and standard deviation of these three experiments. In the absence of a biosurfactant, zoospores swam for approximately 20 hours.

DETAILED DESCRIPTION

Figure 1A:
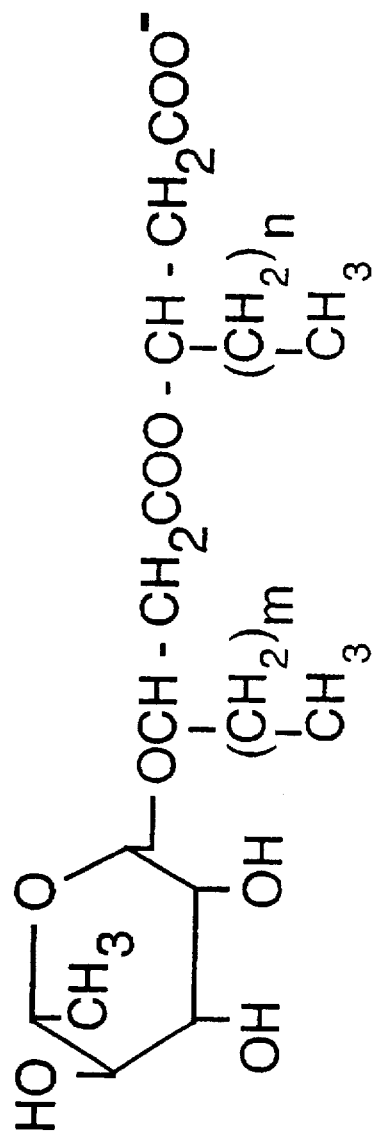
FIG. 1 shows monorhamnolipid (A) and dirhamnolipid (B) structures. Many Pseudomonas spp. produce a mixture of fatty acid tail lengths such that (m+n) may range from 10 to 16 (8).
Figure 1B:
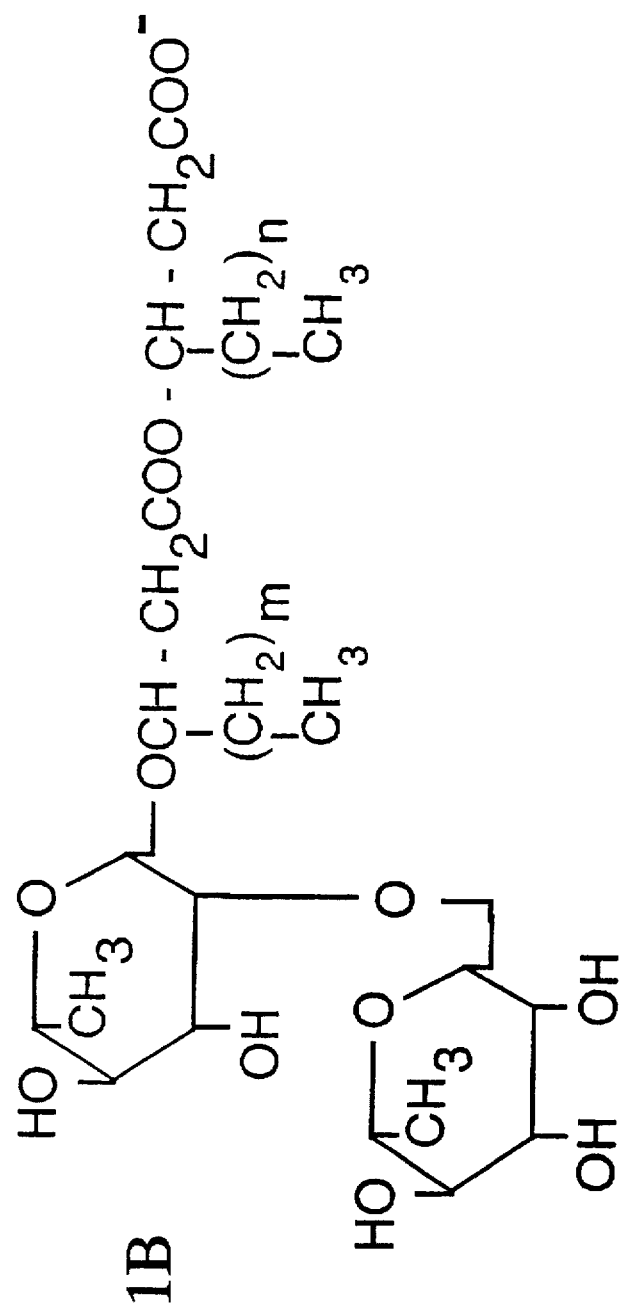

The Pseudomonas strains identified and used according to the subject invention are applied to and will proliferate in the phylloplane of plants intended to be protected from zoosporic plant pathogens. In addition, certain biosurfactants produced by these Pseudomonas strains can be isolated according to the teachings herein set forth, and directly applied to the plant surfaces and plant surroundings where control of zoosporic plant pathogens is desired. The plants can be in the field, in greenhouses, in hydroponic cultivation systems, or any other location where plants desired to be protected are grown. Following are examples which illustrate procedures, including the best mode, for practicing the invention. These examples should not be construed as limiting, for it will immediately be apparent to those of ordinary skill that other Pseudomonas strains could be isolated, cultured, and used in similar ways as taught herein or with routine variation in the specific procedures exemplifying this invention.

EXAMPLE 1

Biosurfactant production.

Production of rhamnolipids by Pseudomonas spp. is strain specific (Table 1). Some strains produce only monorhamnolipid or dirhamnolipid, others produce a mixture, and some strains do not produce rhamnolipids. For example, *Pseudomonas aeruginosa* ATCC 9027, which produces only monorhamnolipid, was obtained from the American Type Culture Collection (Rockville, Md.). The culture was maintained on Pseudomonas agar P (Difco, Detroit, Mich.) slants and transferred monthly. The organism was precultured by inoculating into 25 ml Kay's minimal medium composed of $NH_4H_2PO_4$ (0.3%), $K_2HPO_4$ (0.2%), glucose (0.2%), $FeSO_4$ (0.5 mg-Fe/l), $MgSO_4 \cdot SO_4$ (0.1%) in a 125 ml flask. The preculture was incubated with gyratory shaking at 250 rpm for 24 hours at 37° C., and then 2 ml was used to inoculate 200 ml phosphate-limited preteose peptone/ glucose/ammonium salts medium (PPGAS) in a 1000 ml flask. PPGAS medium is composed of $NH_4Cl$ (0.02 M), KCl (0.02 M), Tris-HCl (0.12 M), glucose (0.5%), preteose peptone (1%), $MgSO_4$ (0.0016 M), adjusted to pH 7.2 (3). This flask was incubated at 37° C. with gyratory shaking at 250 rpm with periodic aseptic removal of samples to monitor surface tension. The initial surface tension of PPGAS medium was 66 dyne/cm. The surface tension of the medium started to decrease at 6 h coinciding with the production of a blue pigment in the culture medium. By 48 h, the surface tension of the medium reached 29 dyne/cm and did not decline further. Rhamnolipid was harvested at 60 h.

Alternatively, some isolates produce biosurfactant when grown on mineral salts medium (MSM) and glucose (2%) or other substrates (see Table 2). MSM is composed of $KH_2PO_4$ (4.5 g/l), $K_2HPO_4$ (9.3 g/l), $NaNO_3$ (2.5 g/l), KCl (1.0 g/l), NaCl (1.0 g/L), $MgSO_4 7H_2O$ (0.4 g/l), $CaCl2H_2O$ (0.05 g/l), $FeCl_3$ (0.001 g/l), $MnSO_4 2H_2O$ (0.0001 g/l). The medium is adjusted to pH 7.0. Isolates are maintained as above and are incubated at 30° C. with gyratory shaking at 250 rpm.

TABLE 1

Quantities of rhamnolipids produced by Pseudomonas spp. isolated from plants.

| Pseudomonas isolate[1] | Isolate source | Rhamnolipid produced[2] | Amount of Rhamnolipid produced[3] (µg/ml) |
|---|---|---|---|
| *P. aeruginosa* $R_5$ | cucumber | mono, di | 1000 |
| *P. putida* $L_1$ | cantaloupe | mono, di | 900 |
| *P. fluorescens* $L_2$ | cantaloupe | mono, di | 500 |
| *P. fluorescens* $R_1$ | tomato | mono, di | 50 |
| *P. fluorescens* $R_2$ | cantaloupe | none | none |
| *P. fluorescens* $R_3$ | cantaloupe | mono, di | 50 |
| *P. fluorescens* $R_4$ | cantaloupe | mono, di | 500 |

[1] Pseudomonas spp. were isolated by imprinting leaves (L) or roots (R) from the indicated plants on King's Medium B agar. Isolates were identified using API-20 strips and Biolog.
[2] Each Pseudomonas isolate was grown in a mineral salts medium (11) with 2% glucose to the stationary phase at room temperature. Rhamnolipids were extracted from the culture supernatant and analyzed by thin layer chromatography (8).
[3] The amount of rhamnolipid produced was estimated from the mass of the recovered biosurfactant from a 200 ml culture.

TABLE 2

Influence of carbon source in production of rhamnolipid by *P. fluorescens* R4

| Carbon Source (2%) | Biomass Produced Dry Weight (mg/mL) | Rhamnolipid Produced (mg/mL) |
|---|---|---|
| glucose | 1.5 ± 0.2 | 2.8 ± 0.1 |
| glycerol | 1.3 ± 0.1 | 0.44 ± 0.04 |
| sucrose | 0.045 ± 0.0045 | -0- |
| α-mannitol | 0.98 ± 0.11 | 0.28 ± 0.03 |
| fructose | 0.53 ± 0.04 | 0.045 ± 0.004 |
| D-sorbitol | no growth | -0- |
| soybean oil | 2.8 ± 0.2 | 1.1 ± 0.1 |
| olive oil | 2.8 ± 0.1 | 3.0 ± 0.6 |

EXAMPLE 2

Rhamnolipid ex traction and measurement.

Rhamnolipid was recovered from the culture supernatant after removal of cells by centrifugation at 6,800×g for 20 minutes. Rhamnolipid was then precipitated by acidification of the supernatant to pH 2.0, followed by centrifugation at 12,100×g for 20 minutes. The precipitate was dissolved in 0.05 M bicarbonate (pH 8.6), then reacidified and centrifuged for a second time at 12,100×g for 20 minutes. Following centrifugation, the precipitate was extracted with chloroform: ethanol (2: 1) three times. The organic solvent was evaporated on a rotoevaporator and the yellowish oily residue was dissolved in 0.05M bicarbonate (pH 8.6). Biosurfactant concentration was then estimated independently by surface tension measurement and by L-rhamnose determination.

Surface tension was measured by using a Fisher (Pittsburgh, Pa.) surface tensiometer (Model 21), that employs the du Nouy ring method. The sensitivity of surface tension measurement was less than 1 mg/l rhamnolipid between 0 and 50 mg/l, and measurements were found to be reproducible to ±0.1 dyne/cm. Rhamnolipid was also quantified by measurement of L-rhamnose using the 6-deoxyhexose method (2). Briefly, biosurfactant solutions were treated with 70% sulfuric acid and boiled for 10 minutes. After the samples were cooled, thioglycolic acid was added to a final concentration of 0.059%. Samples were incubated in the dark for 3 hours followed by spectrophotometric measurement at 420 nm. Standard curves were prepared with L-rhamnose obtained from Sigma (St. Louis, Mo.).

EXAMPLE 3

Rhamnolipid purification.

Components in the partially purified rhamnolipid can be analyzed by thin layer chromatography (TLC) using a chloroform-methanol-water (65:25:4) solvent system. The plate is sprayed with anthrone reagent to allow detection of the rhamnolipids. The monorhamnolipid has an $R_f$ value of 0.72, while the dirhamnolipid has an $R_f$ value of 0.46.

To further purify rhamnolipid, the partially purified material is dissolved in 1 ml of chloroform and applied to a Silica Gel 60 (Alodrich, Milwaukee, Wis.) chromatography column (17×1.5 cm). The column is in all cases first eluted with chloroform to remove the yellow pigment associated with the partially purified rhamnolipid. Then for monorhamnolipid alone, the column is eluted with chloroform:methanol (9:1). For dirhamnolipid alone, the column is eluted with 2:1 chloroform methanol. For mono- and dirhamnolipid mixtures, the column is eluted first with 9:1 chloroform:methanol, and then with 2:1 chloroform methanol. We have found that there is usually some contaminating monorhamnolipid with the dirhamnolipid fraction in mixtures. Individual components can be further analyzed by fast atom bombardment (FAB) mass spectrometry. Purified rhamnolipid can be quantified by weight and rhamnose determination.

EXAMPLE 4

Purified rhamnolipids were tested for zoosporicidical activity. As shown in FIG. 2, the purified rhamnolipids are capable of rapidly lysing zoospores in vitro. Efficacy of rhamnolipids was tested against three representative genera of zoosporic plant pathogens; *Pythium aphanidermatum*, *Plasmopara lactucae-radicis*, and *Phyiophthora capsici*. Exposure of zoospores of all three genera to each biosurfactant at concentrations ranging from 25 to 60 µg/ml caused cessation of motility and lysis of the entire zoospore population in less than 1 minute. In contrast, in the absence of a biosurfactant, zoospores of each species swam for approximately 20 hours. At lower biosurfactant concentrations, the rapidity of loss of motility and subsequent lysis varied depending upon the susceptibility of the various species of pathogen evaluated. The most sensitive pathogen was *P. lactucae-radicis* whose zoospores ceased motility and lysed within 1 minute after exposure to 5.0 µg/ml of each rhamnolipid type. For *P. aphanidennatum* and *P. capsici* the lowest effective biosurfactant concentration ranged from 15 to 25 µg/ml. For these two organisms, the dirhamnolipid was slightly more effective than the monorhamnolipid in causing zoospore lysis. When the two rhamnolipid types were presented in a mixture, the effects were found to be approximately additive.

EXAMPLE 5

General field application of rhamnolipid-producing bacteria

For field applications, the Pseudomonas strains will be applied to the phylloplane of the plant intended to be protected from zoosporic pathogens. The persistence of the Pseudomonas strains in the phylloplane will provide for long-term protection of the vegetation, although repetitive administrations may be required from time to time. The organisms may be applied by spraying, soaking, or the like. Where administered in the field, generally concentrations of the organism will be from $10^6$ to $10^{10}$ cells/ml, and the volume applied per hectare will be generally from about 0.1 oz. to 2 lbs. or more. Where administered to a plant part, the concentration of the organism will usually be from $10^3$ to $10^6$ cells/cm$^2$. Adjustment of concentrations is merely optimization of the procedures taught herein for a variety of circumstances and conditions, all of which is routine to those of ordinary skill in the art.

For commercial formulations, the organisms may be maintained in a nutrient medium ideally at a concentration from $10^5$ to $10^9$ cells/ml prior to application.

To assist in spreading the organisms, they may be formulated with typical stickers, spreaders, and adjuvants generally utilized in agricultural applications, as is well known to those skilled in the art. The cells can be formulated for use in the environment in a variety of ways. They can be applied as wetable powders, granules, pellets, slow-release tablets, or dusts by mixing with various inert materials, such as inorganic minerals (phyllosilicates, carbonates, sulfates, or phosphates) or botanical materials (powdered corn cobs, rice hulls, or walnut shells). Alternatively, the cells can be applied by mixing an organic substrate such as glucose, olive oil, or other compounds which assist proliferation of Pseudomonas or increased production of rhamnolipids. The formulations can include not only spreader/sticker adjuvants, but also stabilizing agents, other additives active against zoospores. Liquid formulations can be aqueous-based or not aqueous and employed as foams, gels, suspensions, emulsifiable concentrates, and the like. The formulations can be applied to the environment to be protected by spraying, dusting, sprinkling, or the like.

EXAMPLE 6

Foliar application of rhamnolipid-producing bacteria.

Ideally, for foliar pathogen control, rhamnolipid-producing Pseudomonas strains can be applied directly to the foliar surfaces. Pepper leaves sprayed to run-off with Pseudomonas in liquid formulation have exhibited colonization of all leaves with a minimum 14-day persistence.

EXAMPLE 7

Direct foliar application of purified rhamnolipids for control of zoosporic plant pathogens.

The purified rhamnolipids themselves can be produced and formulated into a liquid, a slow release pellet, or a granular product by means well known in the art. The latter formulations can be applied directly to the leaf surface. Solubilization during rain or irrigation releases the active product during a time which coincides with the production of the zoospores, thereby providing control.

EXAMPLE 8

Application of rhamnolipid-producing bacteria in greenhouse operations or under field conditions for the control of root diseases caused by zoosporic plant pathogens.

Ideally, *Pseudomonas fluorescens* R$_4$, and alternatively, other rhamnolipid-producing Pseudomonas strains, can be added directly to the nutrient solution via placement in the reservoir servicing a hydroponic unit, or in irrigation water and delivered to the roots of plants via drip-irrigation systems which are extensively employed in open-field agriculture. Additionally, a substrate (organic food source) can be added at the same time to enhance biosurfactant production by the bacterium as described above.

EXAMPLE 9

Root application of rhamnolipid-producing bacteria.

Biosurfactants can be used to control root rot of pepper caused by *Phytophthora capsici* in recirculating hydroponic cultural systems. In the absence of biosurfactant-producing bacteria, all plants within the recirculating hydroponic system were killed within 2 weeks following inoculation of *P. capsici* onto a single plant. Amendment of the nutrient solution with rhamnolipid-producing strains of Pseudomonas by the addition of $10^6$ cells/50 liters resulted in the elimination of the spread of zoospores via the recirculating nutrient solution and control of the disease.

EXAMPLE 10

Application of purified rhamnolipids for control of root-infecting zoosporic plant pathogens.

The purified rhamnolipids themselves can be produced and formulated into liquid, a slow release pellet, or a granular product as taught herein and by means well known in the art. The formulations can be applied directly to the soil surface or added to the irrigation water. Solubilization during rain or irrigation releases the active product during a time which coincides with the production of the zoospores, thereby providing control.

EXAMPLE 11

Root application of purified rhamnolipids.

Biosurfactants can be used to control root rot of cucumber caused by *Pythium aphanidermatum* in recirculating hydroponic cultural systems. In the absence of surfactant, all plants within the recirculating hydroponic system were killed within 5–6 weeks following inoculation of *P. aphanidermatum* onto a single plant. Amendment of the nutrient solution with 20 µg/ml of the purified rhamnolipids, resulted in the elimination of the spread of zoospores via the recirculating nutrient solution and control of the disease.

EXAMPLE 12

Alternative Procedures

In alternative embodiments of the foregoing procedures, any biosurfactant-producing Pseudomonas strain can be used according to the teachings herein and as routinely modified or optimized by ordinary skill.

In general, the biosurfactant-producing bacteria can be formulated as a liquid suspension, a slow release pellet, or a granular product which may include an organic substrate for enhanced biosurfactant production. Additionally, the biosurfactant-producing bacterium could be formulated as above as a "immobilized" product. For soil applications, the above formulations, in addition to being delivered via the irrigation water or nutrient solution, can be injected into the soil either as a pre- or post-plant treatment. The above formulations can also be applied as a foliar application either in the greenhouse or in the field.

Similarly, the biosurfactants themselves can be applied as a liquid formulation, or formulated as a slow release pellet or granular product and delivered to plans as a foliar or soil application as described above.

*Pseudomonas fluorescens* strain $R_4$ has been deposited with the ATCC. The subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

1. Hornby, D. Ed., (1990) *Biological Control of Soil-Borne Plant Pathogens.* (CAB International, Wallingford).
2. Buczacki, S. T. Ed. (1983) *Zoosporic Plant Pathogens. A Modem Perspective.* (Academic Press, London).
3. Stanghellini, M. E., J. A. Tomlinson (1987) *Phytopathology* 77:112.
4. Tomlinson, J. A., E. M. Faithful (1979) *Ann. Appl. Biol.* 93:13.
5. Rosenberg, E. (1986) *CRC Crit. Rev. Biotechnol.* 3:109.
6. Herman, D. C., J. F. Artiola, R. M. Miller (1995) *Environ. Sci. Technol.* 29:2280.
7. Miller, R. M. (1995) *Environ. Health Perspec.* 103:59.
8. Zhang, Y., R. M. Miller (1994) *Appl. Environ. Microbiol.* 60:2101.
9. Becker, Y. O., F. J. Schwinn (1993) *Pestic. Sci.* 37:355.
10. Blakeman, J. B. (1982) *Photopathogenic Prokaryotes, Vol. 1* (Academic Press, London).
11. Guerra-Santos, L. O. Kappeli, A. Fiechter (984) *Appl. Environ. Microbiol.* 48:301.

We claim:

1. A process for controlling zoosporic plant pathogens which comprises contacting said zoosporic plant pathogens with a zoospore-controlling effective amount of a rhamnolipid biosurfactant.

2. The process according to claim 1, wherein the biosurfactant is produced by a Pseudomonas strain.

3. The process according to claim 2, wherein the Pseudomonas strain is *Pseudomonas fluorescens* $R_4$.

4. The process according to claim 1, wherein said rhamnolipid biosurfactant is provided in a liquid.

5. The process according to claim 1, wherein said rhamnolipid biosurfactant is provided in a slow-release pellet.

6. The process according to claim 1, wherein said rhamnolipid biosurfactant is provided in a granular product.

7. The process of claim 4, wherein said liquid is applied to the leaves of the plants.

8. The process of claim 4, wherein said liquid is delivered to the roots of a plant.

9. The process of claim 5, wherein said slow-release pellet is applied to the leaves of a plant.

10. The process of claim 5, wherein said slow-release pellet is applied to the soil surface proximate to a plant.

11. The process of claim 6, wherein said granular product is applied to the leaves of a plant.

12. The process according to claim 6, wherein said granular product is applied to the soil surface proximate to a plant.

13. A process for controlling zoosporic plant pathogen infestation of a plant comprising the steps of providing a live, rhamnolipid-producing strain of Pseudomonas; and applying said Pseudomonas to a plant.

14. The process of claim 13, wherein said Pseudomonas strain is applied to the leaves of a plant.

15. The process of claim 13, wherein said Pseudomonas strain is applied to the roots of a plant.

16. A process for controlling zoosporic plant pathogen infestation of a plant comprising the steps of providing a rhamnolipid biosurfactant, and applying said rhamnolipid biosurfactant to a plant.

17. The process of claim 16, wherein said rhamnolipid biosurfactant is applied to the leaves of a plant.

18. The process of claim 16, wherein said rhamnolipid biosurfactant is applied to the roots of a plant.

* * * * *

UNITED STATES PATENT AND TRADEMARK OFFICE
CERTIFICATE OF CORRECTION

PATENT NO. : 5,767,090
DATED : June 16, 1998
INVENTOR(S) : Stanghellini, et. al.

It is certified that error appears in the above-identified patent and that said Letters Patent is hereby corrected as shown below:

Cover Page, Abstract: "*Pythium aphanidernatum*" should read

--*Pythium aphanidermatum*--.

Column 2, lines 37-38: "Scierospora" should read --*Sclerospora*--

Column 4, line 1: "KCI" should read --KCl--; and line 46: "ex traction" should read --extraction--.

Column 5, line 43: "*Phyiophthora*" should read --*Phytophthora*--; and line 55: "*P. aphanidennatum*" should read --*P. aphanidermatum*--.

Column 7, line 65: after "ATCC" insert -- on January 17, 1996 and assigned accession number ATCC 55734 (American Type Culture Collection, 12301 Parklawn Drive, Rockville, MD 20582 U.S.A)--.

Column 8, line 43: "(984)" should read --(1984)--.

Signed and Sealed this

Twenty-second Day of September, 1998

Attest:

BRUCE LEHMAN

Attesting Officer

Commissioner of Patents and Trademarks